(12) United States Patent
Hachtel et al.

(10) Patent No.: US 6,524,460 B1
(45) Date of Patent: Feb. 25, 2003

(54) METHOD FOR DEFINING THE CHARACTERISTICS OF METAL ELECTRODES OF CERAMIC SENSOR ELEMENTS

(75) Inventors: Hansjoerg Hachtel, Weissach (DE); Jens Stefan Schneider, Anderson, NC (US); Thomas Moser, Schwieberdingen (DE)

(73) Assignee: Robert Bosch GmbH, Stuttgart (DE)

( * ) Notice: Subject to any disclaimer, the term of this patent is extended or adjusted under 35 U.S.C. 154(b) by 129 days.

(21) Appl. No.: 09/693,747

(22) Filed: Oct. 20, 2000

(30) Foreign Application Priority Data

Oct. 22, 1999 (DE) .......................................... 199 51 015

(51) Int. Cl.[7] ................................................ G01B 7/06
(52) U.S. Cl. ......................... 205/81; 205/84; 324/227; 324/230; 427/9; 427/10
(58) Field of Search .............................. 205/81, 82, 84; 427/9, 10; 324/227, 229, 230, 231

(56) References Cited

U.S. PATENT DOCUMENTS

| | | | | |
|---|---|---|---|---|
| 2,751,552 A | * | 6/1956 | Brenner et al. | ............. 324/230 |
| 4,870,359 A | * | 9/1989 | Takahashi | ................... 324/229 |
| 5,731,697 A | * | 3/1998 | Li et al. | ..................... 324/71.5 |
| 5,889,401 A | * | 3/1999 | Jourdain et al. | ............ 324/230 |
| 6,198,278 B1 | * | 3/2001 | Dobler et al. | ............... 324/230 |
| 6,395,161 B1 | * | 5/2002 | Schneider et al. | .......... 204/429 |

FOREIGN PATENT DOCUMENTS

| | | |
|---|---|---|
| DE | 196 52 750 | 7/1998 |
| DE | 198 33 087 | 1/2000 |

* cited by examiner

Primary Examiner—Nam Nguyen
Assistant Examiner—William T. Leader
(74) Attorney, Agent, or Firm—Kenyon & Kenyon

(57) ABSTRACT

A method for defining the characteristics of metal electrodes of ceramic sensor elements, where the metal electrodes are deposited as layers and subjected to a subsequent annealing process. The aim is to provide a non-destructive, simple and economical method, capable of being automated, for performing an acceptance test in a specimen-specific manner on the sensor element. In the case of the test procedure proposed here, the quantity and distribution of gold deposited so as to be inaccessible in the protective layer, are indirectly determined. This is done by measuring the layer thickness during manufacturing of an electrode, in a before/after comparison, with the aid of an eddy-current measuring process where the electrode is placed in the magnetic circuit of a coil that is traversed by the flow of a high-frequency a.c. current, and the resulting ostensible inductance of the coil is measured using an LCR measuring unit. The coil can be wired as a resonant circuit with the aid of a capacitor.

5 Claims, 4 Drawing Sheets

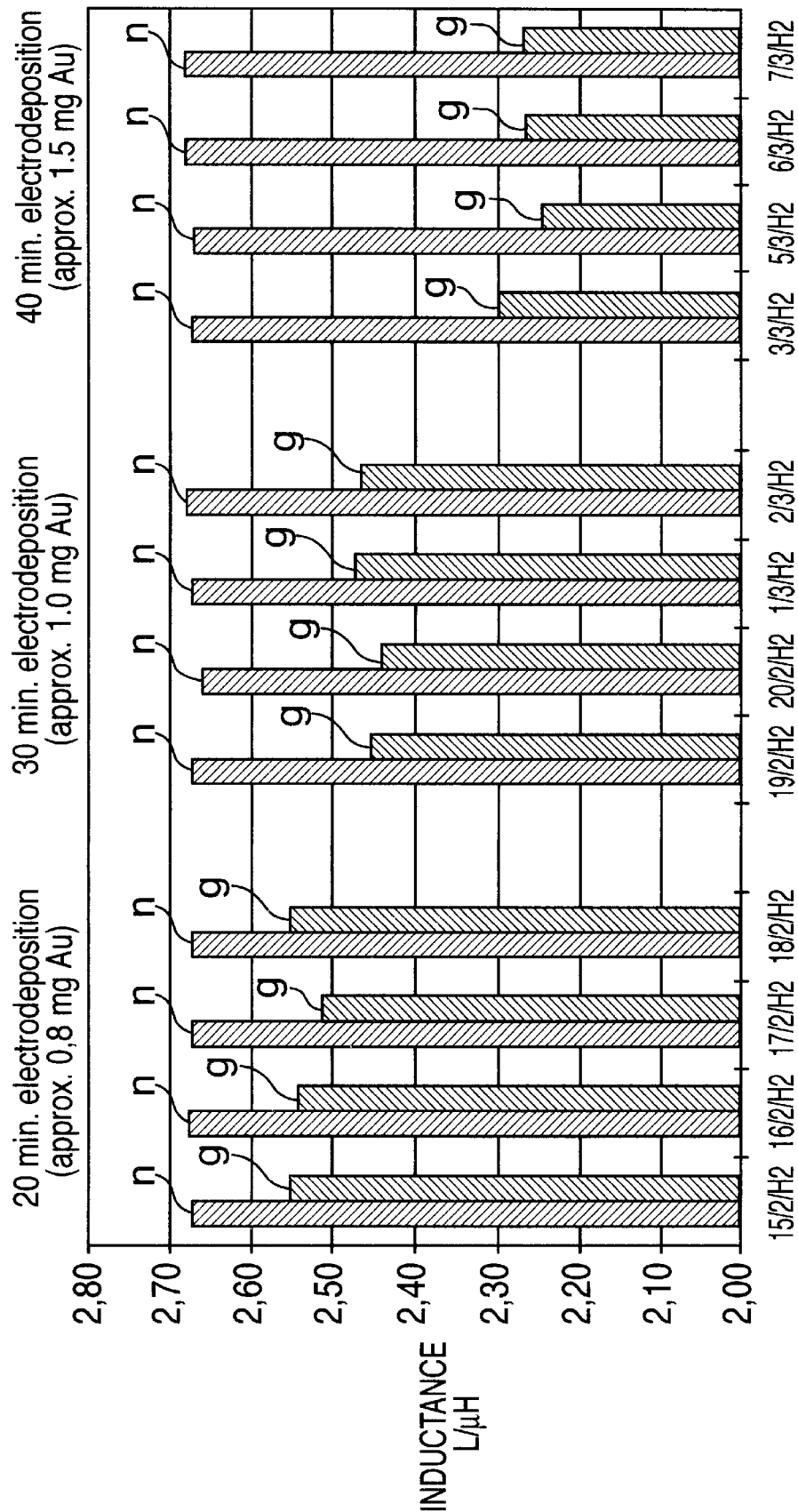

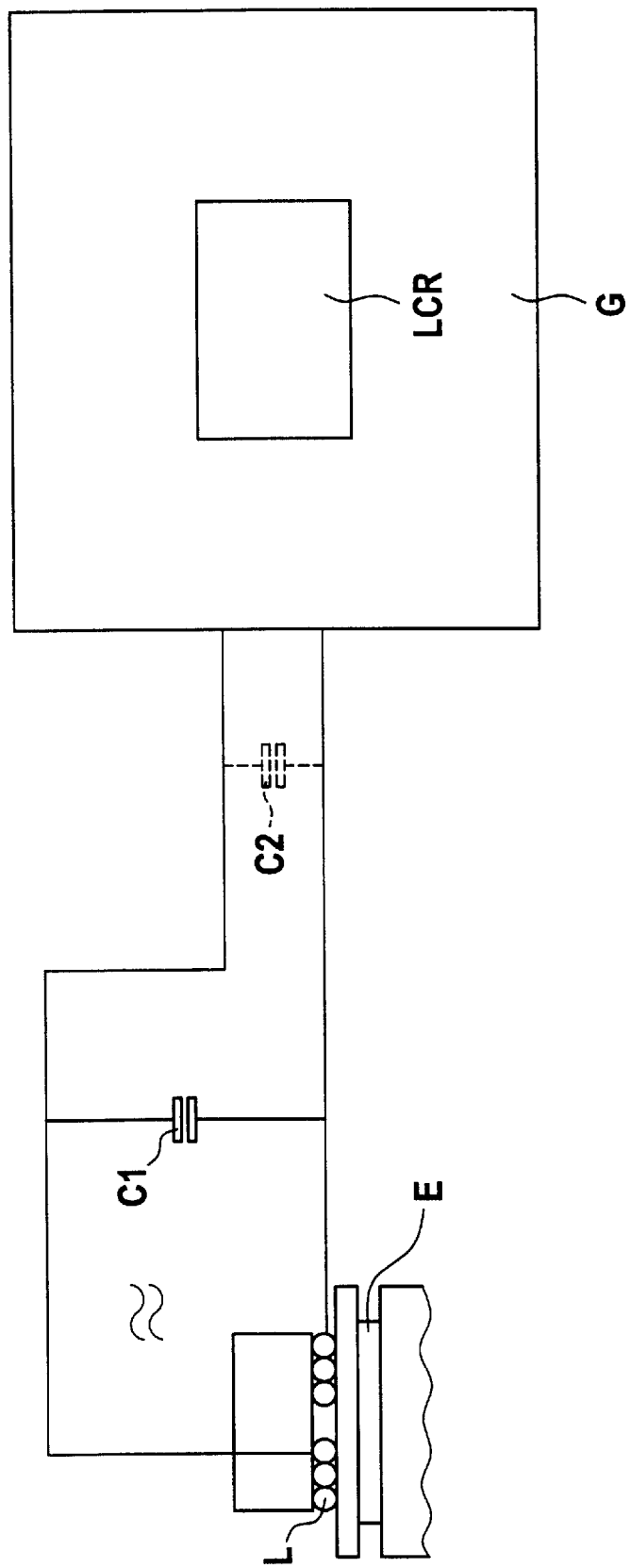

METHOD FOR DEFINING THE CHARACTERISTICS OF METAL ELECTRODES OF CERAMIC SENSOR ELEMENTS

FIELD OF THE INVENTION

The present invention relates to a method for defining the characteristics of metal electrodes of ceramic sensor elements, where the metal electrodes are deposited as layers and subjected to a subsequent annealing process, and the electrode layers to be defined are placed in the magnetic field of an a.c. current-carrying measuring coil, which detects the electrical and, if indicated, the magnetic properties of the layers to be evaluated, in the magnetic field, and analyzes them with respect to specific criteria, and to a device for implementing the method.

BACKGROUND INFORMATION

A method of this kind discussed in German Published Patent Application No. DE 196 52 750 A is already being successfully used in the batch testing of a galvanically chromium-plated cassette for a valve device. Using an eddy-current measuring method, one can determine the thickness of a layer of electrically conductive material, in this case of a chromium layer, for purposes of manufacturing control.

In the manufacturing of a ceramic hydrocarbon sensor of the firm Robert Bosch GmbH, the outer electrode is fabricated by a subsequent galvanic gold plating of a sintered Pt cermet electrode located underneath a porous protective layer (see German Published Patent Application No. DE 198 33 087 A). In this electroplating step, approximately 1 to 2 mg of atomic gold are deposited within the porous protective layer and subsequently sintered. The quantity of the deposited gold and the manner in which it is distributed during the sintering process substantially determine the functional properties of the sensor.

The electroplating process can be checked using a non-destructive measuring method, such as analytical balancing (0.1 mg accuracy), current-time measurement (coulomb metric measurement) during electroplating, which is only possible given a high current gain with respect to the Au3+-reduction, or through electrolytic testing using a peroxo compound.

The possible measuring methods named above are either not precise enough, not adequately developed, or encumbered with disadvantages.

SUMMARY OF THE INVENTION

The object of the present invention is to render possible a non-destructive, simple and economical method, capable of being automated, for defining the characteristics of metal electrodes of ceramic sensor elements, where the electrodes are deposited in layers and subjected to a subsequent annealing process, which will enable the distribution and quantity of the deposited metal to be controlled when manufacturing ceramic sensor elements of this kind.

In the case of the method proposed here, the deposited $Au^0$-quantity (that is not accessible in the protective layer) is indirectly determined. This is accomplished by a layer-thickness determination in a before/after comparison with the aid of an eddy-current measuring method.

The method according to the present invention makes it possible to distinguish among uncoated, coated, and annealed sensor ceramics. As a result, an acceptance test can be automatically performed on the electroplating process in a series production, and the deposited gold quantity can be indirectly determined.

Assuming sufficient accuracy, the test value also permits direct inferences to be made with respect to the sensor function/characteristics state, which, after all, depend directly on the quantity and distribution of the deposited gold.

In the case of gas sensors having a complex design, such as an NOx dual-chamber sensor, given a high-level of accuracy of the method according to the present invention, there is the possibility of using specific frequencies to detect and test deeper electrode layers.

The entire measuring sequence carried out using the method according to the present invention is simple, fast, and capable of being fully automated.

BRIEF DESCRIPTION OF THE DRAWINGS

FIG. 2A depicts inductance values, detected as measuring signals, of the measuring coil for various specimen of a hydrocarbon probe, as shown in FIGS. 1A–1C, before the galvanic gold deposition (n) and after the galvanic deposition of gold (g), respectively, using the deposition time duration as a parameter according to the present invention.

FIG. 3 depicts a measuring device set up for carrying out the inductance measurements according to the present invention.

DETAILED DESCRIPTION

Figure 1:
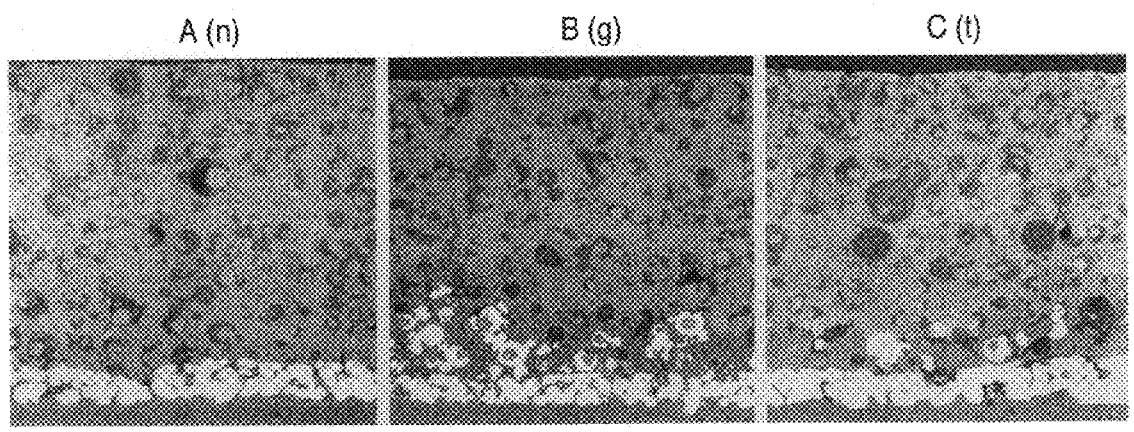
FIGS. 1A–1C show cross-sectional views, produced by a scanning electron microscope, of a hydrocarbon sensor element having a Pt cermet electrode, prior to the galvanic gold deposition, after the galvanic gold deposition, and following the annealing process, respectively, according to the present invention.

This test procedure indirectly determines the (inaccessible) $Au^0$ quantity deposited in the protective layer of a hydrocarbon solid-state sensor. This is done by measuring the layer thickness during the before/after comparison and by determining the mixed crystal formation and distribution, likewise in the before/after comparison. For this, an eddy-current measuring process is used, where the hydrocarbon solid-state sensor, cited as an example, is subjected during manufacturing of the metal electrodes, in a specimen-specific manner, first to a reference measurement (n) without a gold electrode layer and then to a subsequent measurement (g) with a deposited gold electrode layer. From the difference between the measuring signals detected during the reference measurement (n) and the subsequent measurement (g), one is able to derive, in each case, a value indicating the thickness or quantity of the deposited atomic gold.

During the further course of the procedure, the annealing process is followed by a further measurement (t) on the annealed gold electrode. From the difference in the measuring signals recorded between the subsequent measurement (g) and the further measurement (t) following the annealing procedure, one is able to derive a value indicative of the mixed crystal formation and distribution of the deposited gold.

The specific inductance values of the a.c. current-carrying measuring coil are recorded as measuring signals in the measuring steps.

Illustrated in FIG. 3 is a measuring device for implementing the measuring method in accordance with the present invention. In this context, sensor element E is placed in the magnetic circuit of measuring coil L, which is traversed by a high-frequency a.c. current and which, together with a capacitor C1, forms a parallel-resonant circuit. Instead of separate capacitor C1, lead capacitor C2 of the supply lead from an LCR measuring unit G to measuring coil L can also be used.

Inductance values are preferably measured in an LCR measuring bridge G. If, in the process, the measured values obtained in the measurements do not suffice to perform a measured-value analysis (the magnitude of the measuring effect depends on the size of the sensor and the quantity of the deposited gold), then coil L, as shown in FIG. 3, is wired to a parallel-resonant circuit.

The inductance of the sensor coil configured in the parallel-resonant circuit is preferably likewise measured by an LCR measuring bridge. The capacitance of the resonant circuit shown in FIG. 3 can, as mentioned, be applied both from a separately mounted capacitor C1, or from a connecting cable of suitable length having a capacitor C2.

As measuring signals, the ostensible inductance values of sensor coil L determined by the measuring bridge are recorded in the measuring steps. Measurements are preferably made with the same measuring frequency in all measuring steps.

FIGS. 1A, 1B and 1C show greatly enlarged photographs in cross-section, as taken by a scanning electron microscope, of a sensor element designed for detecting HC hydrocarbon and having a PT/Au electrode. FIG. 1A shows the sensor element having a Pt cermet electrode disposed on a substrate and a relatively thick, porous $ZrO_2$ protective layer arranged thereon, and, in fact, prior to the deposition of the atomic gold. FIG. 1B shows the same sensor element following the galvanic deposition of the atomic gold, which is initially deposited on the surface of the porous $ZrO_2$ protective layer, but also penetrates to some degree into the porous $ZrO_2$ protective layer.

FIG. 1C shows the same sensor element following the annealing process, which results in atomic gold penetrating further into the porous $ZrO_2$ protective layer and in mixed crystal being formed. The annealing step leading to the cross-sectional image of FIG. 1C was carried out at approximately 1200° C. for four hours in air. (In FIGS. 1A, 1B and 1C, 1 cm corresponds to 10 $\mu$m).

It should be mentioned that the sensor electrode shown in FIG. 1C represents the actual mixed potential electrode of the hydrocarbon sensor.

Graphically in the form of specimen-specific bar charts, FIG. 2A demonstrates that the method according to the present invention makes it possible to determine with sufficient accuracy the gold quantity precipitated right through the $ZrO_2$ protective layer. Varying electrodeposition times, namely 20 minutes, 30 minutes and 40 minutes resulted in different $Au^0$ quantities being deposited in the different specimen, $15/2/H_2$–$18/2/H_2$; $19/2/H_2$, $20/2/H_2$; $1/3/H_2$, $2/3/H_2$; $3/3/H_2$, $5/3/H_2$, $6/3/H_2$, $7/3/H_2$. Plotted on the ordinate is the inductance L in $\mu$H of the measuring coil connected to a capacitor in a resonant circuit obtained in each reference measurement prior to the electrodeposition and in each subsequent measurement following the electrodeposition. Without the electrodeposition, inductance values of between 2.6 and 2.7 $\mu$H were obtained. Following the galvanic gold deposition, inductance values were obtained of between 2.5 and 2.6, between 2.4 and 2.5, and between 2.2 and 2.3 $\mu$H, in conformance with the varying electrodeposition times. The measured values of the individual specimen are denoted with n prior to the galvanic gold deposition in FIG. 2A, and following the galvanic gold deposition with g. In this context, following a 20-minute galvanic gold deposition, the inductance values denoted with g correspond to an $Au^0$ quantity of approximately 0.8 mg, following a 30-minute galvanic gold deposition to an $Au^0$ quantity of approximately 1.0 mg, and following a 40-minute galvanic gold deposition to an $Au^0$ quantity of approximately 1.5 mg. These approximate quantitative values are able to be defined for the deposited gold in an analytical balancing operation.

FIG. 2A clearly shows that the inductance values and thus the deposited gold quantities that ensue in the three groups are able to be clearly distinguished from one another. This means that the differences between the measured values n and g formed using the eddy-current measuring method in accordance with the present invention yield in an immediately and clearly distinguishable manner a value for each deposited gold quantity.

Figure 2B:
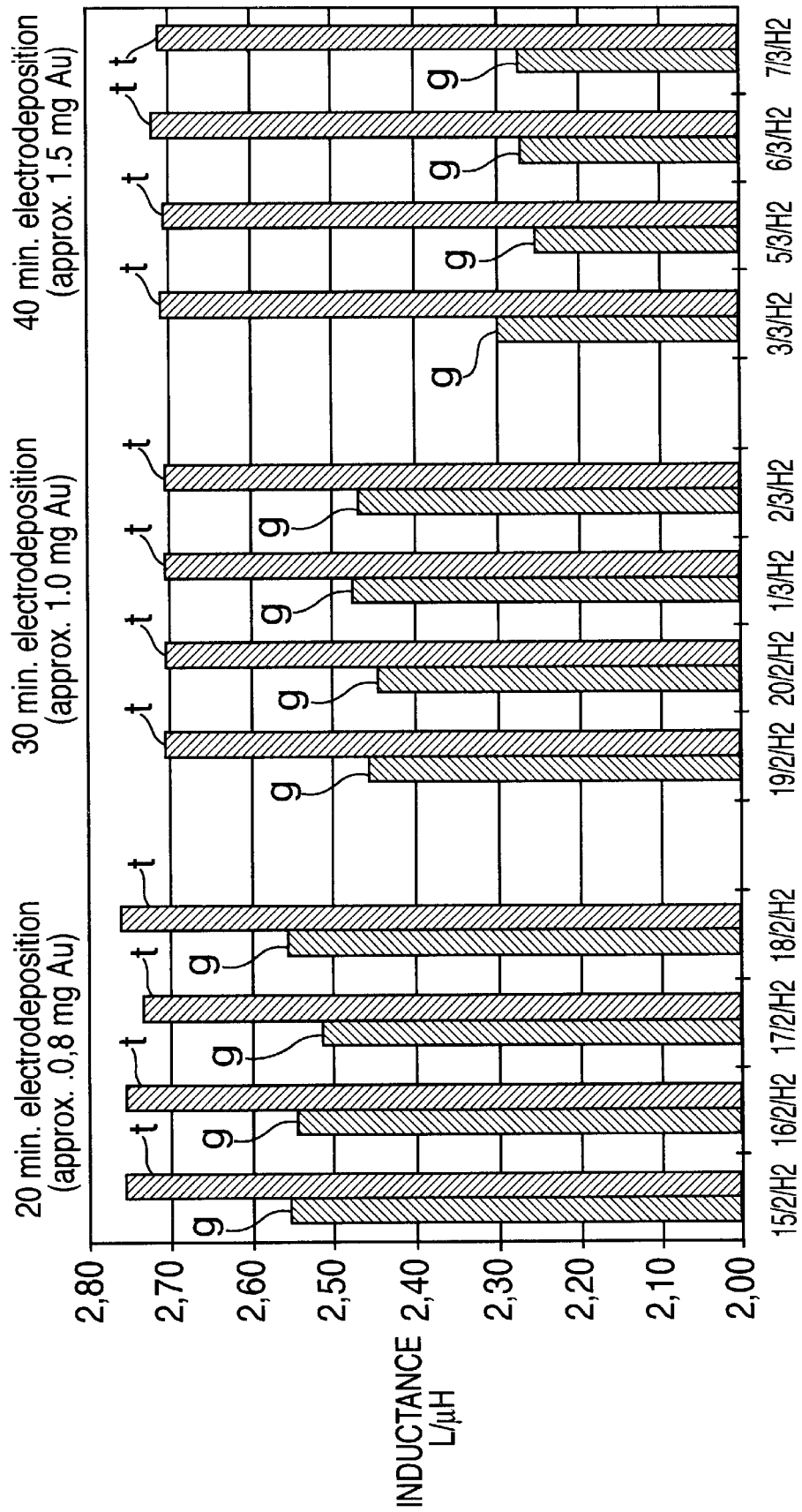
FIG. 2B shows the inductance values of the measuring coil detected as measuring signals, in the case of the same specimen as in FIG. 2A, following the electrodeposition (g) and after the annealing (t), using the deposition time duration as a parameter, according to the present invention.

Plotted again in FIG. 2B are the measured values, designated by g, of the inductance values that were obtained once following the electrodeposition with the three different electrodeposition times. Also depicted graphically as bar charts in FIG. 2B are the measured values denoted by t, following the annealing (in accordance with FIG. 1C) of the same specimen as in FIG. 2A.

The differences (the relative measuring signal) resulting between measured values g and t in accordance with the method of the present invention essentially describe the mixed crystal formation of the Pt/Au layer. The amplitude of this relative measuring signal, when sufficiently accurate, makes it possible to directly infer the sensor function or the characteristics state of the sensor element, since its function and characteristics state are directly a function of the quantity and distribution of the deposited gold.

The inductance values are preferably measured using the LCR measuring bridge (G in FIG. 3). If, in the process, the measured values obtained in the measuring steps do not suffice to perform a measured value analysis (the magnitude of the measuring effect is a function of the size of the sensor and of the quantity of the deposited gold), then, as shown in FIG. 3, the coil is wired into a parallel-resonant circuit.

The inductance of the sensor coil configured in a parallel resonant circuit is preferably likewise measured by the LCR measuring bridge. The capacitance of the resonant circuit can be applied both by a specially mounted capacitor (C1) and/or by a connecting cable (C2) of appropriate length. To achieve a high enough measuring sensitivity to determine these values, the sensor coil is operated with an a.c. current, whose frequency may fulfill two conditions:

1. The level of the coil's a.c. current frequency may only be slightly lower than the resonant frequency of the resonant circuit.
2. The level of the coil's a.c. current frequency may be selected in such a way that the penetration depth of the coil's magnetic field into the measuring object is slightly greater than the thickness of the electrically conductive layers of the electrode to be measured.

As measuring signals, the ostensible inductance values of the sensor coil determined in this manner by the measuring bridge are recorded in the measuring steps. Measurements are preferably made with the same measuring frequency in all measuring steps.

However, in place of the above described inductance values for the measuring coil, one can also retrieve other characteristic values indicative of the measuring coil's magnetic field to obtain the measuring signals.

The measuring sequence of the method in accordance with the present invention derived with the aid of the measuring device depicted in FIG. 3 turns out to be simple and fast and, in addition, is able to be fully automated.

Although the method according to the present invention was described by way of example in an application for measuring the quantity or thickness and distribution of atomic gold subsequently introduced into a porous protective layer of a sintered Pt cermet electrode of a hydrocarbon solid-state sensor, the method according to the present invention is able to be used for inductive (eddy current) layer testing of other sensor elements as well. Possible applications are listed in the following, ranked by increasing stringency of the accuracy requirements:

i) Distinguishing among uncoated, coated, and annealed sensor ceramics (in accordance with FIGS. 1A, 1B and 1C); acceptance test of the electrodeposition step in series production; indirect determination of the deposited metal quantity ($Au^0$).

ii) Given sufficient accuracy, the test value also permits direct inferences to be made with respect to the sensor function/characteristics state, which, after all, depend directly on the quantity and distribution of the deposited metal ($Au^0$).

iii) Given sufficient accuracy of the process, manufacturing tolerances are also able to be recognized and quantified with respect to the layer thickness, cermet structural differences, and phase limits in electrode layers of conventional $\lambda$ probes.

iv) In the case of gas sensors having a complex design, such as NOx dual-chamber sensors, the possibility exists to optionally detect and test deeply lying electrode layers when the method according to the present invention is carried out at specific frequencies.

What is claimed is:

1. A method for determining the characteristics of metal electrodes of a ceramic sensor element, the metal electrodes being deposited as layers, during the manufacturing of the metal electrodes in a specimen-specific manner, comprising the steps of:

placing the ceramic sensor element in a magnetic field of an a.c. current-carrying measuring coil, which is for detecting the electrical and the magnetic properties of the layers to be evaluated in the magnetic field, and for analyzing them with respect to specific criteria;

using the measuring coil to measure the ceramic sensor element having a first metal electrode layer, resulting in a reference measurement;

using the measuring coil to measure the sensor element following a deposition of a second metal electrode layer, resulting in a second measurement;

subtracting to determine a difference between the reference measurement and the second measurement to determine characteristics of at least one of a thickness and a quantity of a deposited metal;

annealing a metal electrode of the sensor element;

using the measuring coil to measure the annealed electrode, resulting in a third measurement; and subtracting to determine a difference between the second measurement and the third measurement to determine characteristics of a mixed crystal formation and distribution resulting from annealing.

2. The method of claim 1, further comprising the step of:

recording specific inductance values of the measuring coil as measuring signals during the measurement steps that result in the reference, second and third measurements.

3. The method of claim 1, further comprising the step of:

recording ostensible inductance values measured using a measurement coil that includes, to enhance measuring sensitivity, a capacitor that is wired to a resonant circuit.

4. The method of claim 3, further comprising the step of:

selecting a level of a measuring frequency such that a penetration depth of the magnetic field is greater than a thickness of electrically conductive layers of the metal electrodes measured.

5. The method of claim 1, further comprising the step of:

measuring at least one of a quantity and a thickness and distribution of atomic gold subsequently introduced into a porous protective layer of a sintered Pt cermet electrode of a hydrocarbon solid-state sensor.

* * * * *

UNITED STATES PATENT AND TRADEMARK OFFICE
CERTIFICATE OF CORRECTION

PATENT NO. : 6,524,460 B1
DATED : February 25, 2003
INVENTOR(S) : Hachtel et al.

It is certified that error appears in the above-identified patent and that said Letters Patent is hereby corrected as shown below:

<u>Column 6,</u>
Line 9, change "the sensor element" to -- the ceramic sensor element --.

Signed and Sealed this

Eleventh Day of May, 2004

JON W. DUDAS
*Acting Director of the United States Patent and Trademark Office*